(12) United States Patent
Verborgt et al.

(10) Patent No.: US 9,193,875 B2
(45) Date of Patent: Nov. 24, 2015

(54) SOLVENT-FREE, SELF-POLISHING POLYURETHANE MATRIX FOR USE IN SOLVENT-FREE ANTIFOULINGS

(75) Inventors: Jozef Verborgt, Tarpon Springs, FL (US); Arthur A. Webb, Fort Washington, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 1183 days.

(21) Appl. No.: 11/183,220

(22) Filed: Jul. 14, 2005

(65) Prior Publication Data
US 2007/0014753 A1  Jan. 18, 2007

(51) Int. Cl.
    C09D 5/16  (2006.01)
(52) U.S. Cl.
    CPC ..................................... *C09D 5/1675* (2013.01)
(58) Field of Classification Search
    CPC ...................................................... C09D 5/1675
    USPC ............................ 523/122; 525/326.8; 528/55
    See application file for complete search history.

(56) References Cited

U.S. PATENT DOCUMENTS

| | | | |
|---|---|---|---|
| 3,012,287 A | 12/1961 | Tucker | |
| 3,265,774 A | 8/1966 | Friedman | |
| 3,354,100 A * | 11/1967 | Kuryla | 521/167 |
| 3,442,827 A | 5/1969 | Friedman | |
| 3,932,339 A | 1/1976 | McLeod | |
| 3,990,381 A * | 11/1976 | Shepherd et al. | 114/67 R |
| 4,130,432 A * | 12/1978 | Wehner et al. | 106/18.31 |
| 4,133,781 A | 1/1979 | Ashida et al. | |
| 4,204,051 A * | 5/1980 | Wellner et al. | 528/55 |
| 4,207,322 A | 6/1980 | von Bebenburg et al. | |
| RE30,698 E | 8/1981 | Elliott et al. | |
| 4,732,929 A * | 3/1988 | Chang et al. | 524/541 |
| 5,958,514 A | 9/1999 | Havey et al. | |
| 5,981,690 A | 11/1999 | Lustig et al. | |
| 6,096,447 A * | 8/2000 | Gan et al. | 429/3 |
| 6,248,806 B1 * | 6/2001 | Codolar et al. | 523/177 |
| 6,592,999 B1 | 7/2003 | Anderson et al. | |
| 2003/0125471 A1* | 7/2003 | Ishihara et al. | 525/326.8 |

FOREIGN PATENT DOCUMENTS

GB    1577715    10/1980

OTHER PUBLICATIONS

Temple C. Patton "Pigment Handbook vol. II: Applications and Markets", John Wiley & Sons, New York , pp. 30-34 and 95-98 (1973).*
STN Search REport p. 1.*
Handbook of Organophosphorous Chemsitry, edited by Robert Engle—Chapter 8 "Some Aspects of H-Phosphonate Chemistry", Marcel Dekker, Inc., New York, New York p. 377-379 (1992).*
PCT Search Report and Written Opinion in PCT/US2006/026835.
Search Results.
Bradley et al., Metal Alkoxides (1978), pp. 27-33, 185-186.
Nawata, "Catalysts for Manufacture of Poly(ethylene terephthalata) with good brightness", SciFinder, 2005, pp. 3-4.
Wright, "Method for Calculating the Boiling Points of Tetraalkoxysilanes and Hexaalkoxydisloxanes", Journal of Chemical and Engineering Data, Apr. 1960, vol. 5, No. 2, pp. 206-220.
Kuznetsova, "Synthesis of Hydroxyalkoxysilanes and urethanes based of them", SciFinder, 2005, pp. 2-3.
Kuznetsova et al, Polyurethane coatings based on tetrakis(B-hydroxyethoxyethoxy)-and dimethylbis(B-hydroxyethoxyethoxy)silanes, Scifinder, 2005, pp. 2-3.
Kopylov et al, "Transesterification of tetraethoxysilane with difunctional alcohols in the presence of nucleophilic catalysts", SciFinder, 2005, pp. 2-3.
Kuznetsova et al, "Effect of the structure of a glycol residue in glycoxysilanes on the properties of polyurethane coatings", SciFinder, 2005, pp. 2-3.
Mairova et al, "Synthesis and properties of boron-urethane-containing epoxy resins and polymers based on them", SciFinder, 2005, pp. 2-4.

* cited by examiner

*Primary Examiner* — Alexander Kollias
(74) *Attorney, Agent, or Firm* — US Naval Research Laboratory; Joseph T. Grunkemeyer

(57) ABSTRACT

A polyol having the formula $X(O-R^1-OH)_m(O-R^2)_nH_q$. X is Si, C, B, Ti, P, Al, Mg, or Ca. Each $R^1$ is derived from dipropylene glycol or tripropylene glycol, and each $R^2$ is an aliphatic group. m is 2, 3, or 4; n is 0, 1, or 2; and q is 1 or 2 when X is C, and is 0 when X is not C. A thermoset formed by reacting a polyisocyanate with the polyol. An antifouling coating containing the thermoset and optionally a biocide. An antifouling coating that is not foam formed by reacting $Si(O-R^1-OH)_m(O-R^2)_nR^3$ with a polyisocyanate. Each $R^3$ is an alkyl group or aromatic group.

14 Claims, No Drawings

SOLVENT-FREE, SELF-POLISHING POLYURETHANE MATRIX FOR USE IN SOLVENT-FREE ANTIFOULINGS

BACKGROUND OF THE INVENTION

1. Field of the Invention

The invention relates generally to polyurethane coatings possibly useful as antifouling coatings.

2. Description of the Related Art

Today's modern self-polishing systems are solvent based and are based on either tributyl tin methacrylate copolymers, tributyl silyl methacrylate copolymers or copper acrylate copolymers. A second technology is largely based on wood rosin chemistry and is supposed to replenish the surface by a kind of ablative action. Tributyl tin methacrylate copolymers are being phased out due to environmental considerations. These polymers were the workhorse for the marine industry for the last 25 years.

Tributyl silyl methacrylate copolymers have the advantage of being totally free of any heavy metals. They are however extremely expensive and this has slowed down their acceptance in the very competitive marine market.

Copper acrylate copolymers do function very well and can be produced competitively but suffer from high leaching rates of copper ions which will eventually lead to a phasing out. Ablative antifoulings are also based on the release of copper ions and might have to be phased out as well for environmental considerations.

All the above-mentioned technologies are solvent based and it will be extremely difficult to meet the ever-increasing limitations on solvent emissions. Only the silyl acrylate technology allows for formulations to be free of any heavy metal ions and to formulate totally biodegradable antifoulings.

The marine market needs longer lasting antifoulings that will allow longer dry docking intervals. This currently requires the use of multiple coats of antifouling, which leads to longer drying times and mechanically weaker films due to solvent entrapment, which are subject to mechanical damage.

SUMMARY OF THE INVENTION

The invention comprises a polyol comprising the formula $X(O-R^1-OH)_m(O-R^2)_nH_q$. X is selected from the group consisting of Si, C, B, Ti, P, Al, Mg, and Ca. Each $R^1$ is an independently selected divalent radical derived from dipropylene glycol or tripropylene glycol, and each $R^2$ is an independently selected aliphatic group. m is 2, 3, or 4; n is 0, 1, or 2; and q is 1 or 2 when X is C, and is 0 when X is not C.

The invention further comprises a thermoset formed by reacting a polyisocyanate with the above polyol.

The invention further comprises a process of making a polyol comprising: providing a reactant comprising the formula $X(O-R^2)_rH_q$, and reacting the reactant with a diol comprising the formula $HO-R^1-OH$. X, $R^1$, $R^2$, and q are as defined above. r is 2, 3, or 4.

The invention further comprises a process of making a thermoset comprising: providing the above polyol, and reacting the polyol with a polyisocyanate.

The invention further comprises an antifouling coating comprising a thermoset formed by reacting a polyisocyanate with a polyol. The polyol comprises the formula $Si(O-R^1-OH)_m(O-R^2)_nR^3$. Each $R^1$ is an independently selected divalent radical derived from diethylene glycol or triethylene glycol. Each $R^3$ is an independently selected alkyl group or aromatic group. $R^2$, m, and n are as defined above. The coating is not a foam.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Solvent free antifouling coatings allow the application of single coat films with extremely high film thicknesses allowing possible dry docking intervals of ten or more years. Solvent free coatings can be made to be mechanically much more robust than existing systems, resisting mechanical damages which can be as high as 5% annually. Use of resin systems that are totally free of any heavy metal allows the formulation of antifoulings that are biodegradable and will not leach any harmful metals into the sea environment.

One embodiment is a polyol as described above. The polyol may have a variety of forms including but not limited to the following:

$$X(O-R^1-OH)_m(O-R^2)_n$$

$$X(O-R^1-OH)_m$$

$$Si(O-R^1-OH)_m$$

$$Si(O-R^1-OH)_m R^3$$

$$C(O-R^1-OH)_m H_q$$

The X atom is a central atom having ligands. The R groups need not all be the same. The total of m, n, and q may be equal to the number ligands appropriate for the central atom, such as the valance. For example, when X is Si, C, or Ti, the total of m, n, and q may be 4 (or 3 when there is an $R^3$ group). When X is B, P, or Al the total of m, n, and q may be 3. When X is Mg or Ca m is 2 and n, and q are 0. When X is Si, the polyol may have up to 4 $R^1$ groups, or may have up to 3 $R^1$ groups and an $R^3$ group. When X is C, the polyol may have up to 3 $R^1$ groups, or may have a combination of $R^1$ groups and hydrogens. When X is Si, a suitable average value for m is about 3.3 to about 4. The value of m is a factor in determining the polishing rate. Specific examples include, but are not limited to, the following:

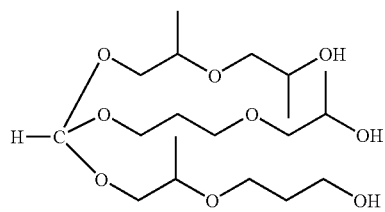

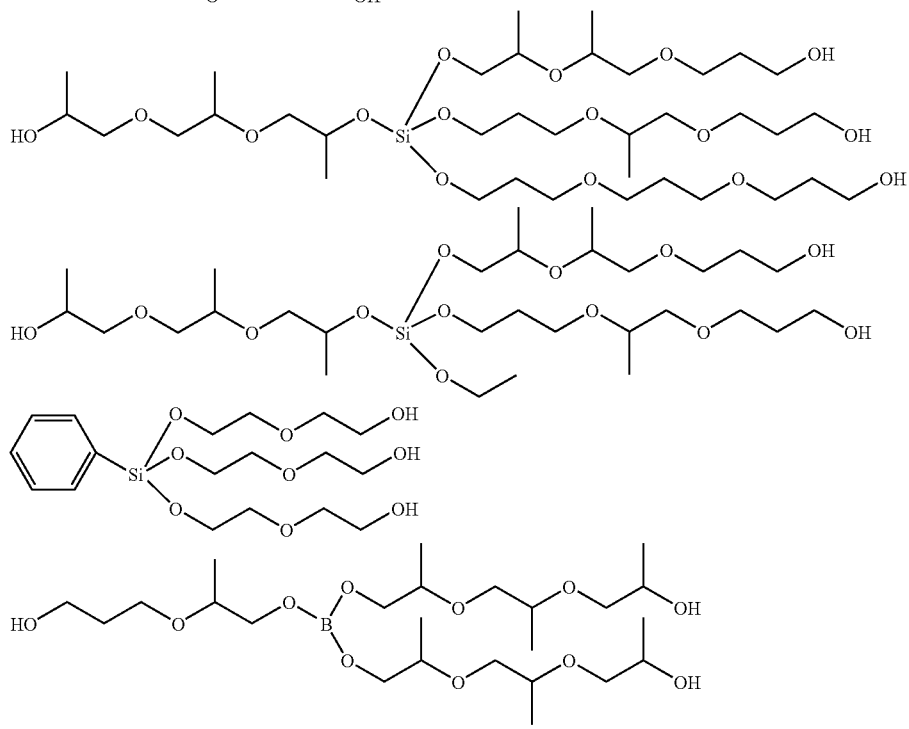

The polyether chains terminated in —OH can be derived from diethylene glycol, triethylene glycol, dipropylene glycol, and/or tripropylene glycol depending on the central atom. Use of these glycols allows for compatibility with isocyanates, as they have a suitable OH equivalent weight. These glycols may, though not necessarily, contain a combination of 1,2- and 1,3-propylene, as shown in the above compounds.

The last compound above is an example of a polyol having both di- and tripropylene glycol groups. The third compound above shows an unreacted ethoxy moiety, the ethyl group being an $R^2$ group. The fourth compound shows an $R^3$ group. The first example above shows a polyol where X is C, m is 3, n is 2, and q is 1. The second example above shows a polyol where X is Si, m is 4, n is 0, and q is 0.

The polyols may be made, among other ways, by a transesterification reaction. The starting reactant has the formula $X(O-R^2)_r R^3_p H_q$. This is reacted with a diol having the formula HO—$R^f$—OH. At least some and potentially all of the $R^2$ groups in the reactant are replaced with $R^1$—OH. The reaction may need to be heated to about 110-200° C. The reaction may be performed with a mixture of reactants and polyols with the possibility of more than one R and $R^1$ groups.

Another embodiment is a thermoset made from the polyol. The thermoset is made by reacting the polyol with a polyisocyanate to form a polyurethane, as shown below for a single ligand.

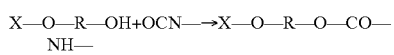

Since a polyol and polyisocyanate is used, the result is a crosslinked thermoset. Suitable polyisocyanates include, but are not limited to, aliphatic polyisocyanate, aromatic polyisocyanate, adducts and prepolymers thereof, and combinations thereof. An example is E744 isocyanate produced by Bayer, which is compatible with most polyols as described herein. The choice is dependent on the compatibility of the polyol with the isocyanate. Compatibility is important because some free glycol may remain in the polyol. Thermosets made from aromatic isocyanates in general may polish faster than those made from aliphatic isocyanates. More than one polyol and/or isocyanate may be used in the reaction.

The reaction may be performed by applying the polyol and polyisocyanate to a surface, substantially in the absence of solvent. This can form a coating that cures quickly at ambient temperatures, even when applied as a single thick coat. A 50/50 weight ratio of polyol to isocyanate may be suitable. The coating may substantially free of air, as opposed to a foam.

The coating may be useful as antifouling coating. A suitable coating may be up to about 50 mil thick and may be applied as a single coat. When exposed to seawater the cured products may hydrolyze at the surface. Silicates may result in a powdery hydrolyzed product which cab be removed by the friction of the water. The formates may form a slimy layer that can be easily removed from the surface, most likely at very low speeds. The thermoset will hydrolyze as shown below for silicon. Similar reactions occur for other central atoms.

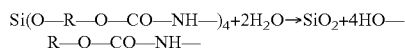

The reaction occurs in the presence of water at varying rates depending on the polyol used. The polishing speed may be regulated by the choice of reactants. One factor is the hydrophobic/hydrophilic balance of the coating. The hydrolysis product may be a small molecule where hydrolysis occurs at each crosslink. The $SiO_2$ is a powder. These products are washed away into the surrounding water, leaving a clean thermoset coating surface behind. The antifouling properties may also be enhanced by including another compound in the coating such as biocide, algaecide, barniclecide, biologically active compound, biological repellant, and combinations thereof. Any biomatter previously attached to the surface may be swept away as the surface hydrolyzes and releases biocides or other compounds.

Triethyl formate may easily be reacted by transesterification with propylene glycols. The reaction may be catalyzed by acids such as phosphoric acid or p-toluene-sulfonic acid. The resulting polyols are usually tri-functional and can be cured with either aliphatic or aromatic isocyanates. Depending on the glycols and isocyanates compatible mixtures that can be cured at any desirable speed may be obtained. The resulting coatings can be made to be rubbery, resilient, or extremely hard. As the systems are totally solvent free they can be applied at almost any film thickness without the normal risk of solvent entrapment.

When exposed to seawater these coatings do develop surface hydrolysis over time and as such replenish their surface continuously. The speed of polishing or surface hydrolysis can be regulated by either increasing the steric hindrance of the formate functional group or by changing the hydrophobic/hydrophilic balance of the total system. The products generated by the hydrolysis are organic, slimy in nature, and easily removed from the surface. Moreover they are biodegradable in the surrounding seawater.

The preferred methods of controlling the polishing speed are the variation of the equivalent hydroxyl number of the polyol or alternatively the addition of a retarder polyol. Both methods result in a different weight percentage of hydrolyzable content in the coating and as such allow a fine control of the polishing speed.

Tetraethyl silicate or ortho silicate may be reacted by transesterification with glycols or polyols to form higher weight polyols. The reaction can be catalyzed by acids or bases and by catalysts such as titanates of dibutyl tin laurates.

The resulting polyols are usually tetra-functional and depending on the glycols that are used can be made compatible with either aliphatic or aromatic isocyanates. They can be cured at almost any speed to form either rubbery, resilient, or extremely hard and tough coatings.

The silicate ester functionality within the polyol will undergo a slow hydrolysis reaction, which will lead to surface polishing and replenishment of the surface. The hydrolysis product is a powdery material that can easily be removed from the surface by the mechanical friction of the seawater.

It is possible to control the surface polishing or hydrolysis reaction by either changing the steric hindrance at the silicate ester function or alternatively by changing the hydrophobic/hydrophilic balance of the resin system. This can be done by either changing the equivalent hydroxyl number of the polyol or by adding a non-hydrolyzable "retarder" polyol to the curing mixture. Both methods result in a different weight percentage of hydrolyzable content in the cured resin system.

Borates, phosphites, and titanates can be transesterified with glycols and polyols in the same way as the silicate esters. The resulting polyols may be more water sensitive and require a different balance in the hydrophobic/hydrophilic balance in order to obtain useful products.

Alkoxides of magnesium, calcium, aluminum, and other polyfunctional alkoxides may be reacted with glycols and polyols to form polyols that contain hydrolyzable functional groups. Again these polyols are much more water sensitive and do require a totally different hydrophobic/hydrophilic balance in order to obtain useful materials for antifoulings.

Having described the invention, the following examples are given to illustrate specific applications of the invention. These specific examples are not intended to limit the scope of the invention described in this application.

EXAMPLE 1

Polyols made from tetra-ethyl ortho silicate—In a three necked one liter flask were added one mole of TEOS (tetra-ethyl ortho silicate (MW 208), four moles of di-propylene glycol (MW 134) and 0.20 grams of sodium metal as catalyst. The temperature was raised and the transesterification reaction started at about 105° C. A total of 4 moles of ethanol were removed over a period of about 2 hours. The end temperature was about 210° C. The reaction product was a low viscous resin, light in color with an OH equivalent weight of 140.

The same procedure was used for the reaction of TEOS with tri-propylene glycol (MW 192). The resulting low viscous resin had an OH equivalent weight of 198.

EXAMPLE 2

Polyols made from tri-ethyl ortho formate—In a three necked flask were added one mole of tri-ethyl ortho formate (MW 148) and three moles of di-propylene glycol (MW 134). 0.3 grams of para toluene sulfonic acid were added as catalyst. The temperature was raised and the transesterification reaction started at about 115° C. The reaction was complete when three moles of ethanol were removed. The end temperature of the reaction was about 210° C. The resulting resin had a very low viscosity, was light in color, and had an OH equivalent weight of 137.

The same reaction was carried out with tri-propylene glycol (MW 192). The resulting resin had an OH equivalent of 193.

EXAMPLE 3

Polyols made from tri-ethyl phosphite—In a three necked flask were added one mole of tri-ethyl phosphite (MW 166) and three moles of di-propylene glycol (MW 134). 0.2 grams of sodium metal were added as catalyst and the reaction temperature was raised. The transesterification reaction starts at about 110° C. The reaction was complete when three moles of ethanol were removed by distillation. The end temperature of the reaction was about 210° C. The resulting resin had a low viscosity, as light in color, and had an OH equivalent weight of 143.

The same procedure was carried out with tri-propylene glycol (MW 192). The resulting resin had an OH equivalent weight of 201.

EXAMPLE 4

Polyol made from tri-ethyl borate—In a three necked flask were added one mole of tri-ethyl borate (MW 146), three moles of di-propylene glycol (MW 134), and 0.2 grams of sodium metal as catalyst. The reaction temperature was raised and the transesterification reaction started at about 110° C. The reaction was complete when three moles of ethanol were removed by distillation. The end temperature of the reaction was about 210° C. The resulting resin had a low viscosity, was light in color, and had an OH equivalent weight of 137.

EXAMPLE 5

Polyol made from tetra-ethyl ortho titanate—In a three necked flask were added one mole of tetra-ethyl ortho titanate (MW 228), four moles of di-propylene glycol (MW 134), and 0.2 grams of sodium metal as catalyst. The temperature was raised and the reaction started at about 110° C. The reaction was complete when four moles of ethanol were removed by distillation. The end temperature was about 210° C. The resulting resin had a low viscosity, was light in color, and had an OH equivalent weight of 145.

EXAMPLE 6

Thermosets—All polyols can be cured with aliphatic or aromatic di and poly isocyanates. Compatibility was obtained in all cases with Desmodur E744 (Bayer).

14 grams of the polyol made from TEOS and di-propylene glycol were mixed intensively with 17.9 grams of Desmodur E744. 0.1% of dibutyl di-laurate was added as catalyst. Clear films or disks can be cast from this mixture. The cured materials had good mechanical properties and showed a very good resistance when immersed in seawater. Over time however the surface underwent a hydrolysis and turned white. The resulting hydrolysis product was easily removed by rubbing or by moving seawater.

13.7 grams of the polyol made from tri-ethyl ortho formate were mixed with 17.9 grams of Desmodur E744 and 0.1% of dibutyl tin di-laurate as catalyst. Strong resilient sheets and disks were cast from this mixture. Upon exposure in seawater the surface of the thermoset hydrolyzed and a slimy film was formed which was easily removed by moving seawater.

Similar mixtures can be made with all polyols. They can also be pigmented with pigments and fillers that are standard in the coating industry. The mixtures can be formulated as antifouling paints by incorporating bioactive materials such as algicide, barnacle killers and or repellants.

Obviously, many modifications and variations of the present invention are possible in light of the above teachings. It is therefore to be understood that the claimed invention may be practiced otherwise than as specifically described.

What is claimed is:

1. An antifouling self-polishing coating consisting of:
a thermoset hydrolyzable in water formed by reacting an aromatic polyisocyanate with a polyol; and
optionally one or more of a biocide, an algaecide, a barniclecide, a biologically active compound, or a biological repellant,
the polyol is given by the formula:

$X(O-R^1-OH)_m(O-R^2)_nH_q$, wherein: X is selected from the group consisting of Si, C, B, Ti, P, Al, Mg, and Ca;
each $R^1$ is independently a divalent radical derived from dipropylene glycol or tripropylene glycol;
each $R^2$ is independently an aliphatic group;
m is 2, 3, or 4;
n is 0, 1, or 2; and
q is 1 or 2 when X is C, and is 0 when X is not C.

2. The antifouling self-polishing coating of claim 1, wherein X is C, m is 3,n is 0,and q is 1.

3. The antifouling self-polishing coating of claim 1, wherein the biocide, the algaecide, the barniclecide, the biologically active compound, the biological repellant, or a combination thereof are present in the antifouling self-polishing coating.

4. The antifouling self-polishing coating of claim 1, wherein X is selected from the group consisting of Si, B, Ti, Al, Mg, and Ca.

5. The antifouling self-polishing coating of claim 1, wherein each $R^1$ is a divalent radical derived from dipropylene glycol.

6. The antifouling self-polishing coating of claim 1, wherein X is Si, m is 4,n is 0, and q is 0.

7. The antifouling self-polishing coating of claim 6, wherein each $R^1$ is a divalent radical derived from dipropylene glycol.

8. A process of making an antifouling self-polishing coating comprising:
reacting a polyol with an aromatic polyisocyanate on a surface to form an antifouling coating consisting of:
a polyurethane thermoset that is hydrolyzable in water; and
optionally, one or more of a biocide, an algaecide, a barniclecide, a biologically active compound, or a biological repellant, wherein the polyol is given by the formula:

$X(O-R^1-OH)_m(O-R^2)_nH_q$;

wherein: X is selected from the group consisting of Si, C, B, Ti, P, Al, Mg, and Ca;
each $R^1$ is indendently a divalent radical derived from dipropylene glycol or tripropylene glycol;
each $R^2$ is independently an aliphatic group;
m is 2, 3, or, 4;
n is 0, 1, or 2; and
q is 1 or 2 when X is C, and is 0 when X is not C.

9. The process of claim 8, wherein X is C, m is 3, n is 0, and q is 1.

10. The process of claim 8, wherein the polyol and the aromatic polyisocyanate are allowed to cure at ambient temperature.

11. The process of claim 8, wherein X is selected from the group consisting of Si, B, Ti, Al, Mg, and Ca.

12. The process of claim 8, wherein each $R^1$ is a divalent radical derived from dipropylene glycol.

13. The process of claim 8, wherein X is Si, m is 4, n is 0, and q is 0.

14. The process of claim 13, wherein each $R^1$ is a divalent radical derived from dipropylene glycol.

* * * * *